US011819818B2

United States Patent
Bai et al.

(10) Patent No.: US 11,819,818 B2
(45) Date of Patent: *Nov. 21, 2023

(54) ACID/METAL BIFUNCTIONAL CATALYST PRODUCED BY EXTRUSION

(71) Applicant: ExxonMobil Technology and Engineering Company, Annandale, NJ (US)

(72) Inventors: Chuansheng Bai, Phillipsburg, NJ (US); Jihad M. Dakka, Whitehouse Station, NJ (US); Preeti Kamakoti, Berkeley Heights, NJ (US); Aruna Ramkrishnan, Bridgewater, NJ (US); Anjaneya S. Kovvali, Herndon, VA (US); Anita S. Lee, Spring, TX (US)

(73) Assignee: EXXONMOBIL TECHNOLOGY AND ENGINEERING COMPANY, Annandale, NJ (US)

( * ) Notice: Subject to any disclaimer, the term of this patent is extended or adjusted under 35 U.S.C. 154(b) by 145 days.

This patent is subject to a terminal disclaimer.

(21) Appl. No.: 16/947,704

(22) Filed: Aug. 13, 2020

(65) Prior Publication Data
US 2021/0046464 A1 Feb. 18, 2021

Related U.S. Application Data

(60) Provisional application No. 62/886,986, filed on Aug. 15, 2019.

(51) Int. Cl.
*B01J 23/80* (2006.01)
*B01J 29/46* (2006.01)
(Continued)

(52) U.S. Cl.
CPC ............... *B01J 29/46* (2013.01); *B01J 23/80* (2013.01); *B01J 35/023* (2013.01); *B01J 35/026* (2013.01);
(Continued)

(58) Field of Classification Search
CPC ........ B01J 23/80; B01J 29/46; B01J 37/0009; B01J 37/0036; B01J 37/08; B01J 37/12
See application file for complete search history.

(56) References Cited

U.S. PATENT DOCUMENTS 4,423,155 A * 12/1983 Bell .................. B01J 23/80
502/342
5,218,003 A * 6/1993 Lewnard ............ C07C 41/01
518/700
(Continued)

FOREIGN PATENT DOCUMENTS

CN 101485983 A * 7/2009
CN 104646049 A * 5/2015
(Continued)

OTHER PUBLICATIONS

Kamata (Steam Reforming of Dimethyl Ether over Cu/ZnO/ZrO2 and γ-Al2O3 Mixed Catalyst Prepared by Extrusion, Journal of the Japan Petroleum Institute, 51 (3), 157-164 (2008)).*
(Continued)

*Primary Examiner* — Jun Li
(74) *Attorney, Agent, or Firm* — SHOOK, HARDY & BACON L.L.P.

(57) ABSTRACT

A method of producing bifunctional catalysts by extrusion may include mixing an acid catalyst, a metal catalyst, optionally a binder, and a fluid to produce a dough; extruding the dough to form an extrudate; producing a powder from the extrudate; and calcining the powder to produce an acid/metal bifunctional catalyst. Such acid/metal bifunctional catalysts may be useful in, among other things, converting syngas to dimethyl ether in a single reactor.

12 Claims, 4 Drawing Sheets

(51) Int. Cl.

| | | |
|---|---|---|
| *B01J 35/02* | (2006.01) | |
| *B01J 37/04* | (2006.01) | |
| *B01J 37/08* | (2006.01) | |
| *B01J 37/10* | (2006.01) | |
| *B01J 37/00* | (2006.01) | |
| *C07C 41/01* | (2006.01) | |
| *B01J 37/12* | (2006.01) | |

(52) U.S. Cl.
CPC ....... *B01J 37/0018* (2013.01); *B01J 37/0027* (2013.01); *B01J 37/0036* (2013.01); *B01J 37/12* (2013.01); *C07C 41/01* (2013.01)

(56) References Cited

U.S. PATENT DOCUMENTS

| | | | |
|---|---|---|---|
| 5,753,716 A * | 5/1998 | Peng | C07C 41/01 |
| | | | 518/700 |
| 6,069,107 A | 5/2000 | Kuznetsov et al. | |
| 10,160,708 B2 | 12/2018 | Lee et al. | |
| 2006/0120953 A1* | 6/2006 | Okuyama | C07C 29/16 |
| | | | 423/650 |
| 2012/0157554 A1* | 6/2012 | Okuyama | C07C 29/16 |
| | | | 518/700 |
| 2013/0030224 A1 | 1/2013 | Kim et al. | |
| 2013/0211147 A1* | 8/2013 | Cheiky | B01J 29/04 |
| | | | 502/68 |
| 2016/0347906 A1 | 12/2016 | Williams et al. | |

FOREIGN PATENT DOCUMENTS

| | | | | |
|---|---|---|---|---|
| CN | 104069856 B | | 4/2016 | |
| CN | 106536045 A | | 3/2017 | |
| JP | 2003038957 A | * | 2/2003 | |
| WO | WO-2005028104 A1 | * | 3/2005 | ............ B01J 29/04 |
| WO | 2005/046855 A2 | | 5/2005 | |

OTHER PUBLICATIONS

Machine translation of Ma et al. (CN101485983), publication date Jul. 22, 2009.*
Machine translation of Nakamura (JP2003038957) Feb. 12, 2003.*
Machine translation of CN104646049A, Deng et al., publication date May 2015.*
Bae, J.-W., et al., "Coproduction of Methanol and Dimethyl Ether from Biomass-Derived Syngas on a Cu—ZnO—Al2O3/γ—Al2O3 Hybrid Catalyst", Energy and Fuels, vol. 22, No. 1, pp. 223-230 (2008).
Gentzen, M., et al., "Bifunctional catalysts based on colloidal Cu/Zn nanoparticles for the direct conversion of synthesis gas to dimethyl ether and hydrocarbons," Applied Catalysis A: General, vol. 557, pp. 99-107 (Year: 2018).
Gentzen, M., et al., "Bifunctional hybrid catalysts derived from Cu/Zn-based nanoparticles for single-step dimethyl ether synthesis", Catalysis Science & Technology, vol. 6, pp. 1-10 (2016).
Zhang, Q., et al., "Improvement of a Mesh-Type Cu/Ni/γ—Al2O3/Al Catalyst for Steam Reforming of Dimethyl Ether by Metal (Fe, Zn or La) Addition for CO in Situ Removal", Modern Research in Catalysis, vol. 7, pp. 1-16 (Jan. 31, 2018).
Non-Final Office Action dated Apr. 11, 2022 in U.S. Appl. No. 16/993,219, 12 pages.
Non-Final Office Action dated Jul. 21, 2022 in U.S. Appl. No. 16/947,699, 12 pages.
Non-Final Office Action dated Aug. 23, 2022 in U.S. Appl. No. 16/947,701, 10 pages.
Non-Final Office Action dated Sep. 15, 2022 in U.S. Appl. No. 16/947,706, 8 pages.
Notice of Allowance dated Oct. 21, 2022 in U.S. Appl. No. 16/993,219, 9 pages.
Notice of Allowance dated Feb. 8, 2023 in U.S. Appl. No. 16/947,699, 8 pages.
Notice of Allowance dated Feb. 8, 2023 in U.S. Appl. No. 16/947,701, 10 pages.
Notice of Allowance dated Mar. 1, 2023 in U.S. Appl. No. 16/947,706, 11 pages.

* cited by examiner

ACID/METAL BIFUNCTIONAL CATALYST PRODUCED BY EXTRUSION

CROSS REFERENCE TO RELATED APPLICATIONS

This application claims priority to U.S. Provisional Application Ser. No. 62/886,986 filed Aug. 15, 2019, which is herein incorporated by reference in its entirety.

FIELD

The present disclosure relates to catalysts for direct conversion of syngas to dimethyl ether.

BACKGROUND

Various processes have been proposed for producing dimethyl ether from natural gas. One such process involves co-feeding natural gas with an enriched oxygen stream to an autothermal reformer to produce syngas. Dimethyl ether may then be produced in a two-stage process. In a first stage, methanol is synthesized from the syngas. In the methanol synthesis step, un-reacted gas from the methanol synthesis reactor may be recycled back to the reactor, thereby acting as a syngas quench cooler. The recycle ratio (recycle gas to syngas feed gas) can be quite high in commercial practice, such as from 3:1 to 7:1, due to equilibrium limitations in methanol conversion. In the second stage, methanol is fed to a dimethyl ether reactor where dimethyl ether and water are produced. Water is separated from dimethyl ether is a subsequent stage.

Air separation (for providing an enriched oxygen feed), autothermal reforming, and substantial internal product recycle imposes significant operating and equipment costs for conventional systems for producing dimethyl ether from natural gas. It would therefore be desirable to provide new integrated processes for the production of dimethyl ether from natural gas.

A newer method has been developed for a one-stage process of converting syngas to dimethyl ether. The newer method uses two separate catalysts in a single reactor to convert CO and $H_2$ to methanol with a metal catalyst and the methanol to dimethyl ether with an acid second catalyst. However, the two catalyst being present together and mixed causes catalyst deactivation over time. For example, the acid catalysts produce coke that deactivates the metal catalysts. Further, the metal from the catalysts tends to migrate under reaction conditions preferentially to the acid sites of the acid catalysts and poison or deactivate the acid portion of the bifunctional catalyst.

SUMMARY

The present disclosure relates to bifunctional catalysts and methods of producing such bifunctional catalysts by extrusion.

A method of the present disclosure may comprise: mixing an acid catalyst, a metal catalyst, a fluid, and optionally a binder to produce a dough; extruding the dough to form an extrudate; producing a powder from the extrudate; and calcining the powder to produce an acid/metal bifunctional catalyst.

Another method of the present disclosure may comprise: activating an acid/metal bifunctional catalyst in the presence hydrogen at 150° C. to 350° C., wherein the acid/metal bifunctional catalyst has an average diameter of 0.01 μm to 100 μm and comprises an acid catalyst component and a metal catalyst component, wherein the acid catalyst component is selected from the group consisting of a zeolite, an ion exchanged zeolite, a molecular sieve, a metal oxide, and any combination thereof, wherein the metal catalyst component is a M1/M2/A1 catalyst, wherein M1 is selected from the group consisting of Cu, Cr, Ag, Au, Ru, Rh, Pd, Re, Os, Ir, Pt, and any combination thereof, wherein M2 is selected from the group consisting of Ti, V, Cr, Mn, Fe, Co, Ni, Zn, a rare earth metal, a La series metal, a Y series metal, and any combination thereof, and wherein M1 and M2 are different, wherein the acid catalyst is present at 10 wt % to 80 wt % relative to the total solids weight in the dough, wherein the metal catalyst is present at 10 wt % to 80 wt % relative to the total solids weight in the dough, and wherein the binder is present at 10 wt % to 80 wt % relative to the total solids weight in the dough, and wherein a weight ratio of the acid catalyst to the metal catalyst in the dough is about 2:1 to about 1:10, and wherein a weight ratio of the acid catalyst and the metal catalyst combined to the binder in the dough is about 10:1 to about 1:10; and reacting the activated acid/metal bifunctional catalyst with a feedstream comprising hydrogen and carbon monoxide.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The present disclosure relates to bifunctional catalysts and methods of producing such bifunctional catalysts by extrusion. The methods of the present disclosure for making acid/metal bifunctional catalysts in a straightforward manner.

Acid/Metal Bifunctional Catalysts

The acid/metal bifunctional catalysts of the present disclosure are produced by extrusion of acid catalyst particles, metal catalyst particles, and optionally a binder. Generally, in extrusion the individual particles and binder are mixed in a fluid to form a thick paste or dough that is then extruded at elevated temperatures to cause the fluid to evaporate. The binder holds the previous individual particles together to form a single particle that is a acid/metal bifunctional catalyst.

Figure 1:
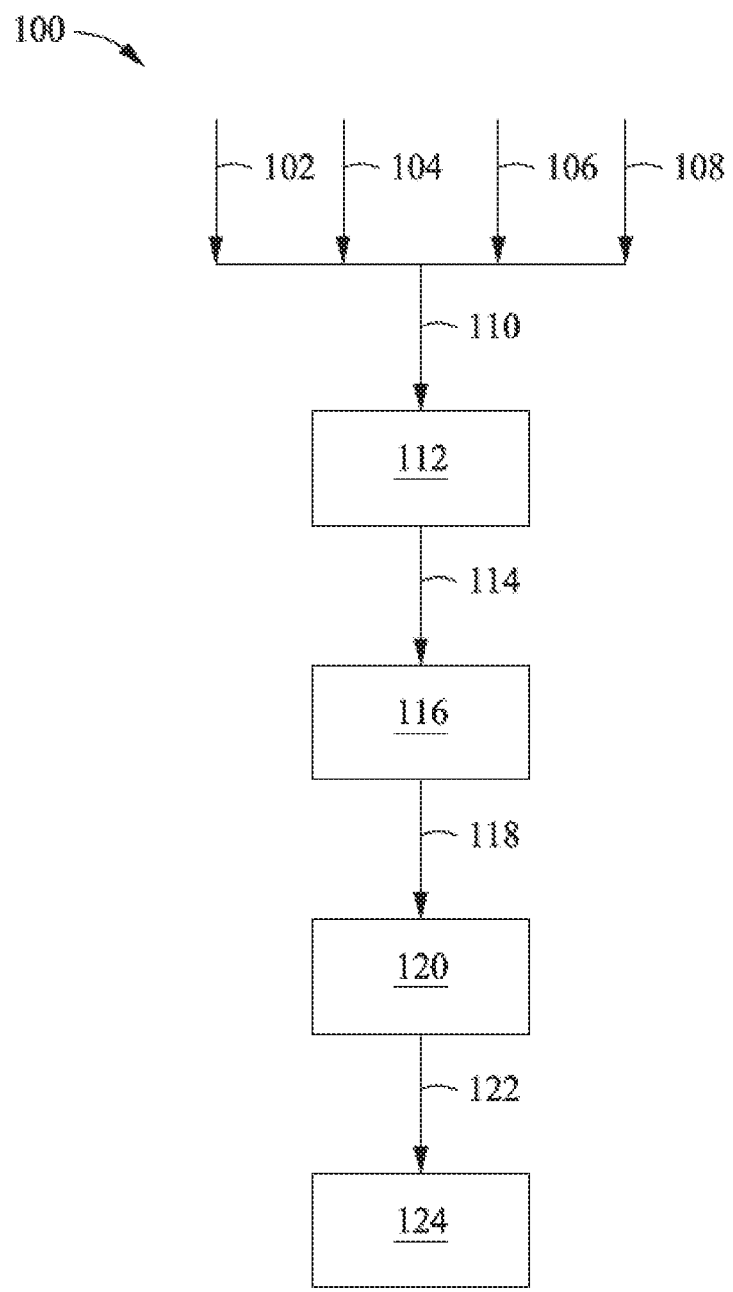
FIG. 1 is a flowchart illustrating an example method of preparing acid/metal bifunctional catalyst.

FIG. 1 is a flowchart illustrating an example extrusion method 100 of preparing acid/metal bifunctional catalyst.

The method includes mixing 110 an acid catalyst 102, a metal catalyst 104, a fluid 106, and a binder 108 to produce a dough 112.

Optionally, the acid catalyst 102, the metal catalyst 104, and/or the binder 108 can be dispersed in the fluid 106 before mixing, in which additional fluid may or may not be needed for producing the dough 112. For example, the acid catalyst 102 may be dispersed in a first fluid and the metal catalyst 104 may be dispersed in second fluid, where the first and second fluids may be the same or different. Then, mixing the acid catalyst 102, the metal catalyst 104, the fluid 106, and the binder 108 may be achieved by adding the acid catalyst 102 dispersed in a first fluid into the metal catalyst 104 dispersed in second fluid, or vice versa, followed by adding the binder to said mixture. Alternatively, only one or two of the acid catalyst 102, the metal catalyst 104, and the binder 108 may be dispersed in a fluid. Then, mixing the acid catalyst 102, the metal catalyst 104, the fluid 106, and the binder 108 may be achieved by adding the remaining components in a dry form into the dispersed component, or vice versa. Alternatively, all of the acid catalyst 102, the metal catalyst 104, and the binder 108 may be dry and added as a mixture or individually to the fluid 106.

The metal catalyst 104 may be present in the dough 112 at about 10 wt % or greater (or about 10 wt % to 80 wt %, or 10 wt % to 25 wt %, or 25 wt % to 50 wt %, or 50 wt % to 80 wt %) based on the total solids weight in the dough 112. The acid catalyst 102 may be present in the dough 112 at about 10 wt % or greater (or about 10 wt % to 80 wt %, or 10 wt % to 25 wt %, or 25 wt % to 50 wt %, or 50 wt % to 80 wt %) based on the total solids weight in the dough 112. The binder 108 may be present in the dough 112 at about 10 wt % or greater (or about 10 wt % to 80 wt %, or 10 wt % to 25 wt %, or 25 wt % to 50 wt %, or 50 wt % to 80 wt %) based on the total solids weight in the dough 112. The fluid 1006 may be present in the dough 112 at about 25 wt % or less (or about 1 wt % to 25 wt %, or 1 wt % to 5 wt %, or 5 wt % to 15 wt %, or 10 wt % to 25 wt %) based on the total weight of the dough 112.

A weight ratio of acid catalyst 102 to metal catalyst 104 in the dough 112 can be about 2:1 to about 1:10, or about 1.5:1 to about 1:5, or about 1:1 to about 1:4. A weight ratio of acid catalyst 102 and metal catalyst 104 combined to the binder 108 in the dough 112 can be about 10:1 to about 1:10, or about 5:1 to about 1:5, or about 3:1 to about 1:3, or about 2:1 to about 1:1, or about 1:1 to about 2:1.

The acid catalyst 102 may be any acid catalyst suitable for converting methanol to dimethyl ether. Generally, the acid property of the acid catalyst 102 may be Lewis acidity, Bronsted acidity, or the combination of the both Lewis acidity and Bronsted acidity. Examples of acid catalysts 102 can include, but are not limited to, a zeolite, an ion exchanged zeolite, molecular sieves (e.g., SAPO), metal oxides (e.g., oxides of aluminum, silicon, zirconium, boron, and combinations thereof like aluminosilicates, boroaluminosilicates, borosilicates, and the like), and any combination thereof. Examples of zeolites can include, but are not limited to, MCM-49, HZSM-5-5B, mordenite, ZSM-35, ZSM-48, ZSM-11, Chabazite, boric acid modified alumina, phosphorus oxide modified alumina, ERS-8, MoPOx, and the like, and any combination thereof. Examples of combinations of acid catalyst include, but are not limited to, $WO_3$, $ZrO_2$, $SiO_2$, resins, metal organic frameworks (MOFs), zeolite imidazolate frameworks (ZIFs), and the like, and any combination thereof.

The metal catalyst 104 may be any metal catalyst suitable for converting CO and $H_2$ to methanol. Examples of metal catalysts 104 can include, but are not limited to, a M1/M2/A1 catalyst, wherein M1 is selected from the group consisting of Cu, Cr, Ag, Au, Ru, Rh, Pd, Re, Os, Ir, Pt, and any combination thereof, wherein M2 is selected from the group consisting of Ti, V, Cr, Mn, Fe, Co, Ni, Zn, a rare earth metal, a La series metal, a Y series metal, and any combination thereof, and wherein M1 and M2 are different.

The binder 108 should be inert in the subsequent reactions of syngas to dimethyl ether. Examples of binders 108 can include, but are not limited to, clay, theta-alumina, delta-alumina, alpha-alumina, silica, titania, zirconia, boric acid, carbon, organic compounds (e.g., polymers), and the like, and any combination thereof.

The acid catalyst 102 may have an average diameter (determined by light scattering) of about 1 μm to about 100 μm, or about 1 μm to about 25 μm, or about 20 μm to about 50 μm, or about 25 μm to about 75 μm, or about 50 μm to about 100 μm. The metal catalyst 104 may have an average diameter (determined by light scattering) of about 0.01 μm to about 10 μm, or about 0.01 μm to about 1 μm, or about 0.1 μm to about 2 μm, or about 1 μm to about 5 μm, or about 2 μm to about 10 μm.

The fluid 106 may be present in the slurry 110 in a sufficient amount to disperse the acid catalyst 102 and the metal catalyst 104 and form the slurry 110. The fluid 106 can be any fluid or mixture of fluids suitable for dispersing the acid catalyst 102, the metal catalyst 104, and the binder 108. Examples of fluids 106 can include, but are not limited to, water, methanol, ethanol, alcohols of $C_1$ to $C_{10}$, oxygenates, and the like, and any combination thereof.

Once the dough 112 is produced, the method may further include extruding 114 the dough 112 to form an extrudate 116. Before and/or during extruding 114, the dough 112 may be heated to facilitate removal of the fluid 106 and forming the extrudate 116. Heating may be to a temperature of about 50° C. to about 120° C. (or about 65° C. to about 100° C., or about 75° C. to about 95° C.). Further, heating may be to a temperature that is within about 20° C. (or about 10° C.) of a boiling point of the fluid 106.

Next, the method 100 includes producing 118 a powder 120 from the extrudate 116. The extrudate 116 may be used as the powder. However, generally, an extrudate's size is large with little surface area. Accordingly, producing 118 a powder 120 may be carried out via grinding, crumbling, ball milling, and the like, and any combination thereof can be used. This advantageously increases the surface area of the particles.

Preferably, the powder 116 comprises the fluid 106 at about 5 wt % or less (or 0 wt % to about 5 wt %, or 0 wt % to about 3 wt %, or about 0.1 wt % to about 3 wt %, or 0 wt % to about 1 wt %).

To reduce the amount of fluid 106 in the extrudate 116 and/or the powder 120, one or both can be dried at elevated temperatures. Such temperatures should be lower than a temperature that would cause significant calcining of the solids. For example, drying may occur in an inert gas (e.g., nitrogen, argon, and the like, and any combination thereof) or oxygen-containing gas (e.g., oxygen, air, oxygen-enriched air, and the like) at temperature of about 50° C. to about 120° C. (or about 65° C. to about 100° C., or about 75° C. to about 95° C.) for a suitable amount of time (e.g., about 10 minutes to about 48 hours, or about 1 hour to about 24 hours, or about 8 hours to about 18 hours) to achieve a desired amount of fluid 106 in the powder 116.

Then, the method 100 includes calcining 122 the powder 120 to produce the acid/metal bifunctional catalyst 124. Calcining 122 may occur in an oxygen-containing gas (e.g., oxygen, air, oxygen-enriched air, and the like) at a temperature of about 200° C. to about 400° C. (or about 250° C. to about 350° C., or about 275° C. to about 375° C.) for any suitable amount of time (e.g., about 10 minutes to about 48 hours, or about 30 minutes to about 24 hours, or about 1 hour to about 12 hours, or about 1 hour to about 6 hours).

The metal catalyst 104 component may be present in the acid/metal bifunctional catalyst 124 at about 10 wt % or greater (or about 10 wt % to 80 wt %, or 10 wt % to 25 wt %, or 25 wt % to 50 wt %, or 50 wt % to 80 wt %) based on the total weight of the acid/metal bifunctional catalyst 124. The acid catalyst 102 component may be present in the acid/metal bifunctional catalyst 124 at about 10 wt % or greater (or about 10 wt % to 80 wt %, or 10 wt % to 25 wt %, or 25 wt % to 50 wt %, or 50 wt % to 80 wt %) based on the total weight of the acid/metal bifunctional catalyst 124. The binder 108 component may be present in the acid/metal bifunctional catalyst 124 at about 10 wt % or greater (or about 10 wt % to 80 wt %, or 10 wt % to 25 wt %, or 25 wt % to 50 wt %, or 50 wt % to 80 wt %) based on the total weight of the acid/metal bifunctional catalyst 124.

A weight ratio of acid catalyst 102 component to metal catalyst 104 component in the acid/metal bifunctional catalyst 124 can be about 2:1 to about 1:10, or about 1.5:1 to about 1:5, or about 1:1 to about 1:4. A weight ratio of acid catalyst 102 component and metal catalyst 104 component combined to the binder 108 in the acid/metal bifunctional catalyst 124 can be about 10:1 to about 1:10, or about 5:1 to about 1:5, or about 3:1 to about 1:3, or about 2:1 to about 1:1, or about 1:1 to about 2:1.

The acid/metal bifunctional catalyst 120 particles may have an average diameter (determined by light scattering) of about 0.01 μm to about 100 μm, or about 1 μm to about 100 μm, or about 1 μm to about 25 μm, or about 20 μm to about 50 μm, or about 25 μm to about 75 μm, or about 50 μm to about 100 μm. Optionally, after the acid/metal bifunctional catalyst 120 is formed, grinding or any suitable method can be used to achieve a desired particle size.

The acidity of the acid/metal bifunctional catalyst 120 particles measured with pyridine for Bronsted acid cites (1545 cm$^{-1}$ and 1450 cm$^{-1}$ infrared spectra bands) and ammonia for Lewis acid cites (1620 cm$^{-1}$ and 1450 cm$^{-1}$ infrared spectra bands) may be cumulatively about 1 site to about 250 sites, or 25 sites to 200 site, or 50 sites to 150 sites.

Direct Synthesis of Dimethyl Ether from Syngas

Figure 2:
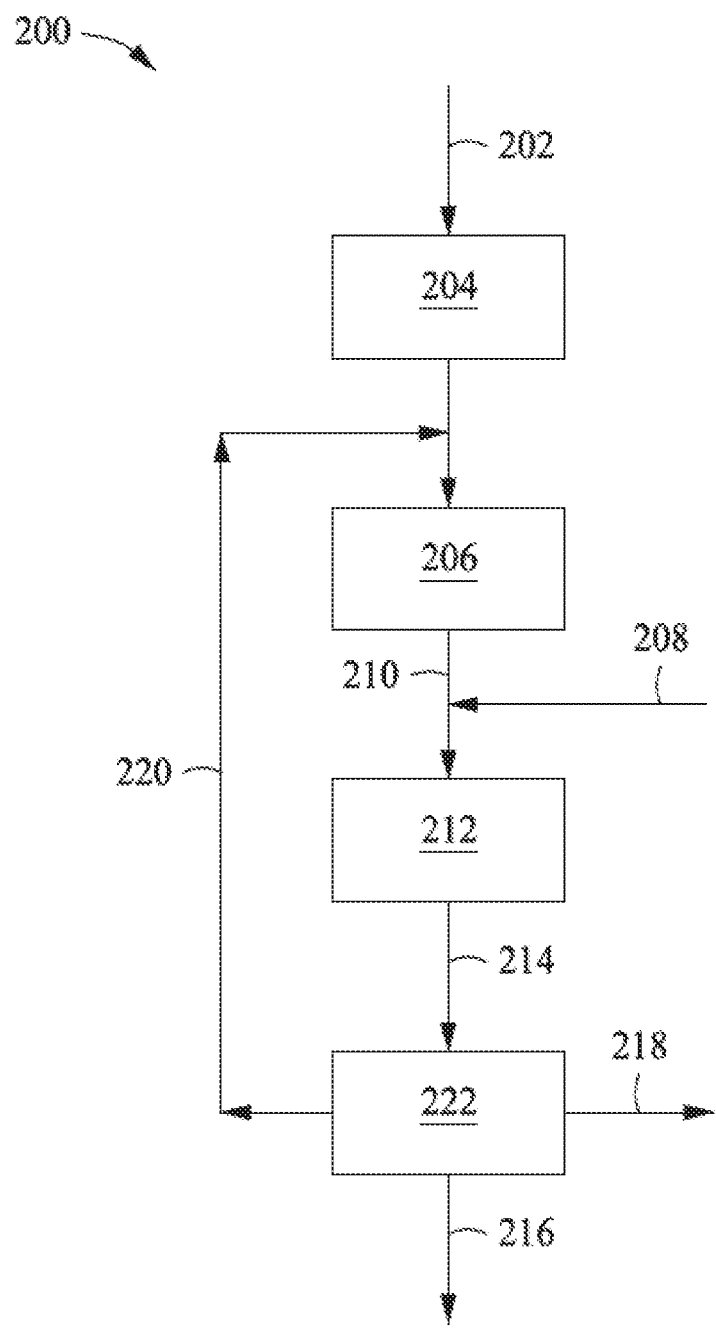
FIG. 2 is a flowchart illustrating an example integrated system and process for producing dimethyl ether from natural gas according to one or more embodiments of the present invention.

An example 200 method and system for the production of dimethyl ether from natural gas is illustrated in FIG. 2. A natural gas stream 202 is fed to a pretreater 204 to remove contaminants such as sulfur, chlorides and olefins. The pretreater 204 may be a single unit or, more likely, it is a series of units for removing the different types of contaminants found in the natural gas stream 204. For example, the pretreater 204 may include a desulfurizing column for removing sulfur. The pretreater 204 can also include a guard bed to remove chlorides and/or a hydrotreater to convert olefins to paraffins.

The pretreated natural gas may then be fed to a reformer 206, which may be a reverse flow reactor, to convert the natural gas to a syngas 210. A recycled $CO_2$ stream 220, which may also include recycled methane, can be fed with the treated natural gas to the reformer 206. It is noted that the pretreated natural gas stream may contain essentially zero $CO_2$ (such as the gas in pipeline gas) or it may have a high $CO_2$ content. Steam may also be added to the reformer 206 to promote the conversion of natural gas to syngas.

Steam 208 and syngas 210 are co-fed to a dimethyl ether reactor 212 to produce a product stream 214, which can include dimethyl ether, carbon dioxide, methane, hydrogen, and other byproducts. The dimethyl ether reactor 212 may operate a temperature of about 200° C. to about 300° C. (or about 230° C. to about 270° C.), a pressure of about 20 bar to about 50 bar (or about 30 bar to about 40 bar), and a gas hourly space velocity (GHSV) of about 1,000 hr$^{-1}$ to about 8,000 hr$^{-1}$ (or about 1,500 hr$^{-1}$ to about 3,000 hr$^{-1}$).

The product stream 214 may be fed to one or more separators 222 to separate the methane, carbon dioxide, and other byproducts 218 from dimethyl ether 216. Methane and carbon dioxide may be recycled back to the reformer 206 via the recycle stream 28. The separation of the products may be accomplished using various separation processes including refrigeration, distillation/fractionation, high-pressure or low-pressure flash separation, or membrane separation.

Prior to running the foregoing method, the acid/metal bifunctional catalyst may be activated by exposure to hydrogen at elevated temperatures (e.g., about 150° C. to about 350° C., or about 200° C. to about 300° C.).

Direct dimethyl ether synthesis may be performed by converting syngas to methanol (Eq. 1) with the in-situ dehydration of methanol to dimethyl ether (Eq. 3). Advantageously, both reactions can occur in the same reactor such that the methanol is nearly instantaneously dehydrated to dimethyl ether as it is produced. In addition, a water gas shift reaction (Eq. 2) is typically present.

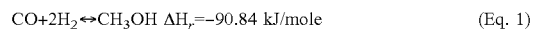

$$CO+2H_2 \leftrightarrow CH_3OH \quad \Delta H_r = -90.84 \text{ kJ/mole} \qquad (Eq. 1)$$

$$CO+H_2O \leftrightarrow CO_2+H_2 \quad \Delta H_r = -41.27 \text{ kJ/mole} \qquad (Eq. 2)$$

The equilibrium of the methanol reaction (Eq. 1) at high temperatures required to promote kinetics, is reactant favored and limits the overall syngas conversion in a traditional methanol process. However, the disclosed acid/metal bifunctional catalyst may enable the in-situ dehydration of methanol immediately after it is formed, which maintains the system sufficiently far from equilibrium limitations of Eq. 1 and may improve the per-pass conversion of syngas.

Various by-products can also be produced during the conversion of syngas to methanol (e.g., methane, water, carbon dioxide, formic acid) and the conversion of methanol to dimethyl ether (e.g., acetates, hydrocarbons, methane, water, and coke). Acetates are known to facilitate metal sintering and metal ion-exchange on the acid catalyst that lead to catalyst deactivation.

Because the addition of steam reduces the per-pass selectivity to dimethyl ether by converting some carbon monoxide to carbon dioxide (Eq. 2), the amount of water present in the dimethyl ether reactor would conventionally be limited to the minimal amounts desired to mitigate coke formation. However, it has been found that the addition of steam in the proposed integrated process can be used to control production of $CO_2$ in the dimethyl ether reactor, which can improve the carbon efficiency of the system or process as described in further detail herein. Furthermore, surprisingly, it has been found that co-feeding steam in such quantities can reduce the selectivity towards hydrocarbons and oxygenates, thereby improving the acid/metal bifunctional catalyst stability.

The total reaction of a system for the synthesis of dimethyl ether (Eq. 4) including the water-gas-shift reaction, methanol synthesis reaction, and dehydration reaction is exothermic.

$$2CH_3OH \leftrightarrow CH_3\text{—}O\text{—}CH_3 + H_2O \quad \Delta H_r = -21.26 \text{ kJ/mole} \quad \text{(Eq. 3)}$$

$$3CO + 3H_2 \leftrightarrow CH_3\text{—}O\text{—}CH_3 + CO_2 \quad \Delta H_r = -246 \text{ kJ/mole} \quad \text{(Eq. 4)}$$

It has been found that carbon efficiency can be improved by controlling feed parameters, particularly the amount of water added to either the reforming reactor or the dimethyl ether reactor. Conventionally, syngas conversion process use factors like $H_2$:CO ratio or M-value, which is $(H_2-CO_2)/(CO+CO_2)$, to define the ideal feed to the syngas conversion reactor. The numerical value selected for this metric typically reflects the ideal stoichiometry for the desired product reaction. Additionally, the presence of water is typically ignored or treated like an inert.

Water, however, plays a critical role in the integrated process described herein. Water may be added in amount to leverage the water-gas-shift reaction to co-produce $CO_2$ (as needed to maximize carbon efficiency) in the dimethyl ether reactor. The amount of water added, is a function of the syngas composition (namely the amount of $CO/CO_2/H_2/H_2O$ present in the feed to the dimethyl ether reactor), which is a function of the steam reforming relative to the dry reforming carried out in the syngas reactor.

A preferred feed to the dimethyl ether reactor may be described with a modified M-value (Mm) per the following equation.

$$Mm = \frac{H_2 - CO_2 + H_2O}{CO + CO_2 - H_2O}$$

Water may be added to the process in total, either in the syngas reactor for steam reforming or in the dimethyl ether reactor. Independent of how the water is split between the reactors this corresponds to a modified M-value of about 1.4 to 1.8 (or 1.5 to 1.7, or 1.6).

Various reforming processes may be employed to produce syngas from such a natural gas feedstream including, but not limited to, partial oxidation, steam methane reforming, autothermal reforming, dry reforming, and the like, and any combination thereof. Preferably, the natural gas stream is reformed using a reverse flow reactor.

Any natural gas feedstream can be reformed into syngas. As used herein, "natural gas" refers to a hydrocarbon feed that is predominantly $C_1$ to $C_4$ hydrocarbons, and it may be predominantly methane. The natural gas feedstream can also include carbon dioxide. For simplicity, examples used herein may make specific reference to methane; however, it should be understood that natural gas feed streams further comprising $C_2$-$C_4$ hydrocarbons may also be used. General equations for the dry reforming and steam reforming for such hydrocarbons are shown in Eq. 5 and Eq. 6, respectively.

$$C_nH_{2n+1} + CO_2 \rightarrow 2nCO + (n+1)H_2 \quad \text{(Eq. 5)}$$

$$C_nH_{2n+1} + H_2O \rightarrow nCO + (2n+1)H_2 \quad \text{(Eq. 6)}$$

In order to improve carbon efficiency of the system, it is desirable to provide a feed of natural gas and carbon dioxide to the reverse flow reactor at a natural gas:carbon dioxide molar ratio of about 1:1, such as about 0.8:1 to about 1.1:1. For example, 2 moles of $CO_2$ and 2 moles of methane may produce 4 moles of CO and 4 mole of $H_2$ as shown in Eq. 7.

$$2CO_2 + 2CH_4 \leftrightarrow 4CO + 4H_2 \quad \text{(Eq. 7)}$$

If the products of Eq. 5 were then fed to the dimethyl ether reactor with steam as a co-feed, the following products would be produced: 1 mole of dimethyl ether, 2 moles of $CO_2$ and 1 mole of $H_2$ (Eqs. 4 and 2).

The reverse flow reactor for reforming the natural gas to syngas may operate at a temperature of about 300° C. and about 1400° C. (or about 500° C. and about 1000° C.) and a pressure range of about 1 bar and about 100 bar (or about 10 bar to about 50 bar).

The effluent from the dimethyl ether reactor may be separated into dimethyl ether, $CO_2$ (optionally with any unreacted $CH_4$, CO, and/or $H_2$), and other byproducts. Any one or combination of separation processes may be employed to perform such separations including, but not limited to, refrigeration, distillation/fractionation, flash separation and membrane separation. The $CO_2$, $CH_4$, and any unreacted intermediates may be recycled as described herein.

Advantageously, recycle streams having desirable compositions can be obtained from separation processes downstream of the dimethyl ether reactor. These recycle streams can be used to improve the carbon efficiency of the integrated system and/or can provide other advantages.

In any embodiment, $CO_2$ and $CH_4$, and optionally CO, recovered downstream of dimethyl ether reactor may be recycled upstream of the syngas generation reactor. The $CO_2$ may be provided in sufficient quantities such that when added to the $CO_2$ native to the natural gas feed will achieve the desired natural gas:carbon dioxide ratio, such as a methane:carbon dioxide molar ratio of about 1:1, such as about 0.9:1.1 to about 1.1:0.9. In some cases, it may be desirable to recycle at least a portion of the $CO_2$ and $CH_4$, and optionally CO and methanol, upstream of the dimethyl ether reactor but downstream of the syngas generator reactor.

Hydrogen may also be recovered from the separation processes and used as fuel. Optionally, at least a portion of the hydrogen can be recycled upstream of the dimethyl ether reactor.

Example Embodiments

A first nonlimiting embodiment of the present disclosure is a method comprising: mixing an acid catalyst, a metal catalyst, a fluid, and optionally a binder to produce a dough; extruding the dough to form an extrudate; producing a powder from the extrudate; and calcining the powder to produce an acid/metal bifunctional catalyst. Optionally, this embodiment may further include on or more of the following: Element 1: wherein producing the powder from the extrudate comprises: drying the extrudate; and grinding the extrudate before or after drying, wherein the powder comprises 5 wt % or less of the fluid; Element 2: the method further comprising: drying the powder; Element 3: the method further comprising: heating the dough while extruding to a temperature within 20° C. of a boiling point of the fluid; Element 4: wherein the acid catalyst is selected from the group consisting of a zeolite, an ion exchanged zeolite, a molecular sieve, a metal oxide, and any combination thereof; Element 5: wherein the metal catalyst is a M1/M2/

A1 catalyst, wherein M1 is selected from the group consisting of Cu, Cr, Ag, Au, Ru, Rh, Pd, Re, Os, Ir, Pt, and any combination thereof, wherein M2 is selected from the group consisting of Ti, V, Cr, Mn, Fe, Co, Ni, Zn, a rare earth metal, a La series metal, a Y series metal, and any combination thereof, and wherein M1 and M2 are different; Element 6: wherein the binder is selected from the group consisting of clay, theta-alumina, delta-alumina, alpha-alumina, silica, titania, zirconia, boric acid, carbon, and any combination thereof; Element 7: wherein the acid catalyst is present at 10 wt % to 80 wt % relative to the total solids weight in the dough, wherein the metal catalyst is present at 10 wt % to 80 wt % relative to the total solids weight in the dough, and wherein the binder is present at 10 wt % to 80 wt % relative to the total solids weight in the dough; Element 8: wherein a weight ratio of the acid catalyst to the metal catalyst in the dough is about 2:1 to about 1:10, and wherein a weight ratio of the acid catalyst and the metal catalyst combined to the binder in the dough is about 10:1 to about 1:10; Element 9: wherein the fluid is selected from the group consisting of: water, methanol, ethanol, and any combination thereof; Element 10: wherein calcining is performed in air at 200° C. to 400° C.; Element 11: wherein the acid/metal bifunctional catalyst has an average diameter of 0.01 μm to 100 μm; Element 12: the method further comprising: activating the acid/metal bifunctional catalyst in the presence hydrogen at 150° C. to 350° C.; and reacting the activated acid/metal bifunctional catalyst with a feedstream comprising hydrogen and carbon monoxide; Element 13: Element 12 and wherein reacting is at a temperature of about 200° C. to about 300° C., a pressure of about 20 bar to about 50 bar, and a gas hourly space velocity (GHSV) of about 1,000 $hr^{-1}$ to about 8,000 $hr^{-1}$; Element 14: Element 12 and wherein the reacting the activated acid/metal bifunctional catalyst with the feedstream is in the presence of steam. Examples of combinations include Element 1 in combination with one or more of Elements 2-14; Element 2 in combination with one or more of Elements 3-14; Element 3 in combination with one or more of Elements 4-14; Element 4 in combination with one or more of Elements 5-14; Element 5 in combination with one or more of Elements 6-14; Element 6 in combination with one or more of Elements 7-14; Element 7 in combination with one or more of Elements 8-14; Element 8 in combination with one or more of Elements 9-14; Element 9 in combination with one or more of Elements 10-14; Element 10 in combination with one or more of Elements 11-14; Element 11 in combination with one or more of Elements 12-14; and Element 12 in combination with one or both of Elements 13 and 14.

A second nonlimiting example embodiment is a method comprising: activating an acid/metal bifunctional catalyst in the presence hydrogen at 150° C. to 350° C., wherein the acid/metal bifunctional catalyst has an average diameter of 0.01 μm to 100 μm and comprises an acid catalyst component and a metal catalyst component, wherein the acid catalyst component is selected from the group consisting of a zeolite, an ion exchanged zeolite, a molecular sieve, a metal oxide, and any combination thereof, wherein the metal catalyst component is a M1/M2/A1 catalyst, wherein M1 is selected from the group consisting of Cu, Cr, Ag, Au, Ru, Rh, Pd, Re, Os, Ir, Pt, and any combination thereof, wherein M2 is selected from the group consisting of Ti, V, Cr, Mn, Fe, Co, Ni, Zn, a rare earth metal, a La series metal, a Y series metal, and any combination thereof, and wherein M1 and M2 are different, wherein the acid catalyst is present at 10 wt % to 80 wt % relative to the total solids weight in the dough, wherein the metal catalyst is present at 10 wt % to 80 wt % relative to the total solids weight in the dough, and wherein the binder is present at 10 wt % to 80 wt % relative to the total solids weight in the dough, and wherein a weight ratio of the acid catalyst to the metal catalyst in the dough is about 2:1 to about 1:10, and wherein a weight ratio of the acid catalyst and the metal catalyst 104 combined to the binder in the dough is about 10:1 to about 1:10; and reacting the activated acid/metal bifunctional catalyst with a feedstream comprising hydrogen and carbon monoxide. This embodiment may optionally further include one or more of the following: Element 15: wherein the acid catalyst is present at 10 wt % to 50 wt % relative to the total solids weight in the dough, wherein the metal catalyst is present at 25 wt % to 80 wt % relative to the total solids weight in the dough, and wherein the binder is present at 10 wt % to 50 wt % relative to the total solids weight in the dough; Element 16: wherein a weight ratio of the acid catalyst to the metal catalyst in the dough is about 1:1 to about 1:5, and wherein a weight ratio of the acid catalyst and the metal catalyst combined to the binder in the dough is about 10:1 to about 1:1; Element 17: wherein reacting is at a temperature of about 200° C. to about 300° C., a pressure of about 20 bar to about 50 bar, and a gas hourly space velocity (GHSV) of about 1,000 $hr^{-1}$ to about 8,000 $hr^{-1}$; and Element 18: wherein the reacting the activated acid/metal bifunctional catalyst with the feedstream is in the presence of steam.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating the invention embodiments disclosed herein are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

To facilitate a better understanding of the embodiments of the present invention, the following examples of preferred or representative embodiments are given. In no way should the following examples be read to limit, or to define, the scope of the invention.

EXAMPLES

Example 1: Catalyst Extrusion

Combinations of metal and acid catalysts were prepared according to the compositions in Table 1. The reference samples were simply the catalyst particles admixed.

Extrusion of CuZnAl/ZSM-5 (75/25) (Catalyst 1): The powders of 25 g of ZSM-5 and 75 g of CuZnAl were placed in a muller and mulled for about 20 minutes. 66.67 g of water was added to the muller and mulled for another 20 minutes. The extrusion dough targeted a solid content of 60 wt %. The extrusion dough was extruded into 1/16 inch quadrilobe extrudates with 1 inch extruder from Diamond America Extruder. After the extrusion, the extrudates of CuZnAl/ZSM-5 (75/25) were spread into thin layers in the sample trays. The extrudates were dried 16 hours in air at 120° C. Then, the extrudates were calcined in air for 3 hrs at 300° C. The calcining furnace was ramped at rate of 2.5° C./min. During the calcination, the air flow was adjusted at 5 volume/volume of solid/minute.

Extrusion of CuZnAl/γ-Al2O3 (75/25) (Catalyst 2): The powders of 34.63 g of VERSAL™-300 $Al_2O_3$ (available from UOP) (solid content 72.2 wt %) and 75 g of CuZnAl were placed in muller and mulled for about 20 minutes. 82.68 g of water was added to the muller and mulled for another 20 minutes. The extrusion dough targeted a solid content of 52 wt %. The extrusion dough was extruded into 1/16 inch quadrilobe extrudates with 1 inch extruder from Diamond America Extruder. After the extrusion, the extrudates of CuZnAl/γ-$Al_2O_3$ (75/25) were spread into thin layers in the sample trays. The extrudates were dried 16 hours in air at 120° C. Then, the extrudates were calcined in air for 3 hrs at 300° C. The calcining furnace was ramped at rate of 2.5° C./min. During the calcination, the air flow was adjusted at 5 volume/volume of solid/minute.

Extrusion of CuZnAl/γ-$Al_2O_3$ (50/50) (Catalyst 3): The powders of 66.40 g of VERSAL™-300 $Al_2O_3$ (solid content 75.3%) and 50 g of CuZnAl were placed in muller and mulled for about 20 minutes. 85.99 g of water was added to the muller and mulled for another 20 minutes. The extrusion dough targeted a solid content of 49.4%. The extrusion dough was extruded into 1/16 inch quadrilobe extrudates with 1 inch extruder from Diamond America Extruder. After the extrusion, the extrudates of CuZnAl/γ-$Al_2O_3$ (50/50) were spread into thin layers in the sample trays. The extrudates were dried 16 hours in air at 120° C. Then, the extrudates were calcined in air for 3 hrs at 300° C. The calcining furnace was ramped at rate of 2.5° C./min. During the calcination, the air flow was adjusted at 5 volume/volume of solid/minute.

Extrusion of CuZnAl/ZSM-5/γ-$Al_2O_3$ (50/25/25) (Catalyst 4): The powders of 25 g of ZSM-5, 33.20 g of VERSAL™-300 $Al_2O_3$ (solid content 75.3%), 50 g of CuZnAl were placed in muller and mulled for about 20 minutes. 73.62 g of water was added to the muller and mulled for another 20 minutes. The extrusion dough targeted a solid content of 55%. The extrusion dough was extruded into 1/16 inch quadrilobe extrudates with 1 inch extruder from Diamond America Extruder. After the extrusion, the extrudates of CuZnAl/ZSM-5 (75/25) were spread into thin layers in the sample trays. The extrudates were dried 16 hours in air at 120° C. Then, the extrudates were calcined in air for 3 hrs at 300° C. The calcining furnace was ramped at rate of 2.5° C./min. During the calcination, the air flow was adjusted at 5 volume/volume of solid/minute.

TABLE 1

|  | Metal Catalyst* | Acid Catalyst* |
| --- | --- | --- |
| Catalyst 1 | 75 wt % CuO/ZnO | 25 wt % ZSM-5 |
| Catalyst 2 | 75 wt % CuO/ZnO | 25 wt % γ-$Al_2O_3$ |

TABLE 1-continued

|  | Metal Catalyst* | Acid Catalyst* |
| --- | --- | --- |
| Catalyst 3 | 50 wt % CuO/ZnO | 50 wt % γ-$Al_2O_3$ |
| Catalyst 4 | 50 wt % CuO/ZnO | 25 wt % γ-$Al_2O_3$ 25 wt % ZSM-5 |

*individual catalyst weight by weight of total catalyst

Example 1: Catalyst Testing

In separate reactions, a reactor was charged with catalyst samples according to Catalysts 1-4 in Table 1 with 125 μm to 160 μm α-$Al_2O_3$ particles above and below the catalysts bed. The catalysts in the reactor were activated by flowing a nitrogen stream comprising hydrogen at 200° C. over the catalyst bed for 120 minutes. Then, the catalyst were used in a syngas to dimethyl ether reaction under the following conditions: a temperature of 230° C. to 270° C., a pressure of 25 bar to 50 bar, and a gas hourly space velocity (GHSV) of 1,000 $hr^{-1}$ to 8,000 $hr^{-1}$. The reaction feed was 37 vol % to 50 vol % $H_2$, 40 vol % to 50 vol % CO, 13 vol % to 40 vol % $CO_2$, 0 vol % to 3 vol % $CH_4$, 5 vol % to 10 vol % Ar (used as an internal standard), and 0 vol % to 10 vol % of $H_2O$. A gas chromatograph fitted with a flame-ionization detector (FID), a thermal conductivity detector (TCD), and optionally a helium ionization detector (HID) (for low water concentrations of 20 ppm to 2 vol %) was used to analyze the product stream.

Figure 3:
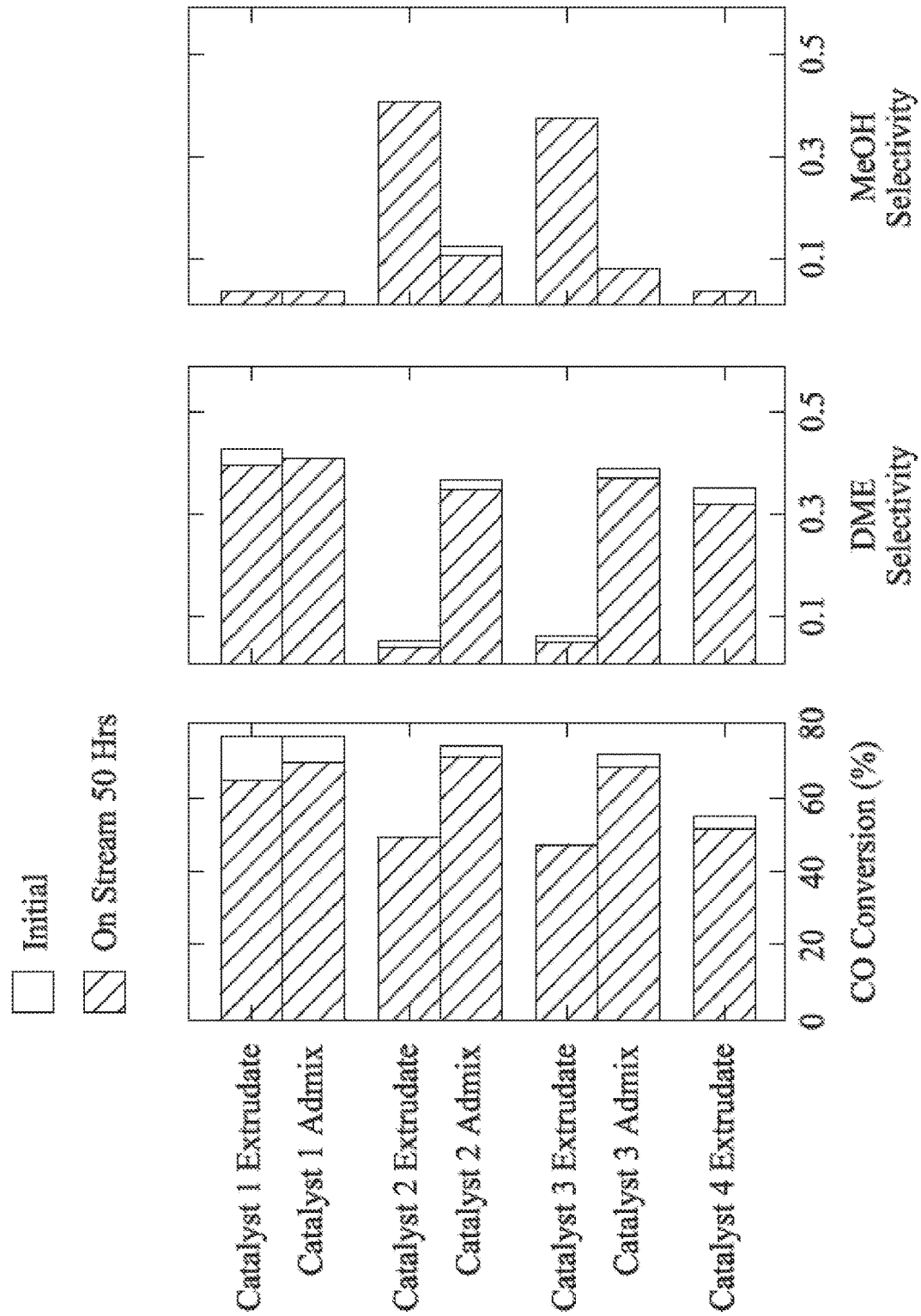
FIG. 3 is a plot of the CO conversion, dimethyl ether selectivity, and methanol selectivity for various catalyst compositions tested both initially and after being exposed to the reactor conditions (or being on stream) for 50 hours.

FIG. 3 is a plot of the CO conversion, dimethyl ether selectivity, and methanol selectivity for the various catalyst compositions tested both initially and after being exposed to the reactor conditions (or being on stream) for 50 hours. Where no initial measurement is obvious in the plots, the initial measurements are comparable to the on stream for 50 hour measurements.

Extruded acid/metal bifunctional catalyst using the ZSM-5 acid catalyst shows comparable activity to the control, admixed sample.

Example 2: Catalyst Extrusion

Combinations of metal and acid catalysts were prepared according to the compositions in Table 2. Catalyst 5 is a reference sample where the catalyst particles admixed. Catalysts 6-8 were extrudate samples prepared by the same methods as Example 1. In these examples, the extruded acid/metal bifunctional catalysts were not further dried before testing their respective activities.

TABLE 2

|  | Metal Catalyst* | Acid Catalyst* |
| --- | --- | --- |
| Catalyst 5 | 75 wt % CuO/ZnO | 25 wt % ZSM-5 |
| Catalyst 6 | 70 wt % CuO/ZnO | 30 wt % ZSM-5 |
| Catalyst 7 | 80 wt % CuO/ZnO | 20 wt % ZSM-5 |
| Catalyst 8 | 50 wt % CuO/ZnO | 50 wt % ZSM-5 |

*individual catalyst weight by weight of total catalyst

Example 2: Catalyst Testing

In separate reactions, a reactor was charged with each of the four catalyst systems with 125 μm to 160 μm α-$Al_2O_3$ particles above and below the catalysts bed. The catalysts in the reactor were activated by flowing hydrogen at 250° C. over the catalyst bed for 120 minutes. Then, the catalyst were used in a syngas to dimethyl ether reaction under the following conditions: a temperature of 230° C. to 270° C., a pressure of 25 bar to 50 bar, and a gas hourly space velocity (GHSV) of 1,000 $hr^{-1}$ to 8,000 $hr^{-1}$. The reaction feed was 37 vol % to 50 vol % $H_2$, 40 vol % to 50 vol % CO, 13 vol % to 40 vol % $CO_2$, 0 vol % to 3 vol % $CH_4$, 5 vol % to 10 vol % Ar (used as an internal standard), and 0 vol % to 10 vol % of $H_2O$. A gas chromatograph fitted with a flame-ionization detector (FID), a thermal conductivity detector (TCD), and optionally a helium ionization detector (HID) (for low water concentrations of 200 ppm to 2 vol %) was used to analyze the product stream.

Figure 4:
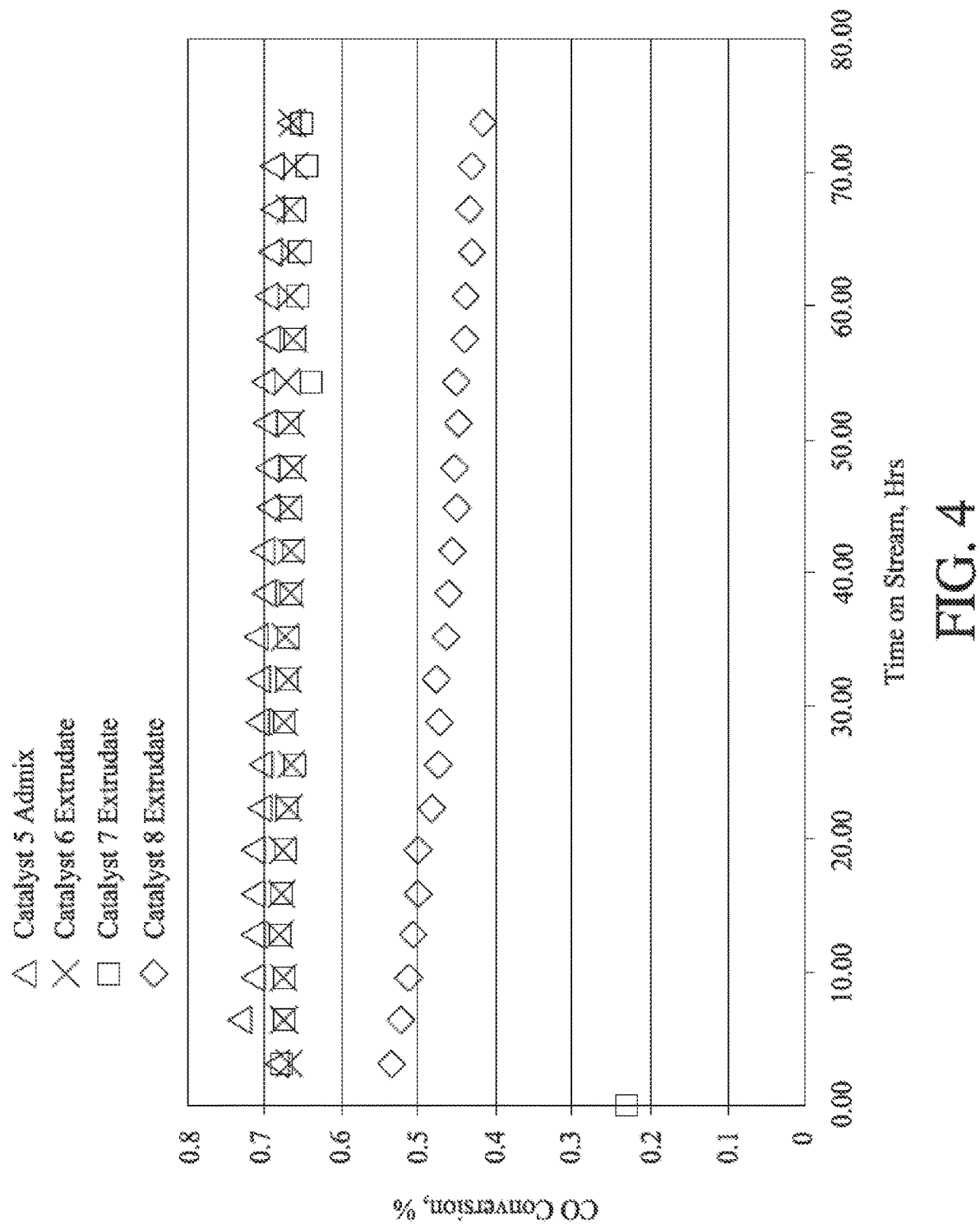
FIG. 4 is a plot of the CO conversion as a function of time being on stream for various catalyst compositions described herein.

FIG. 4 is a plot of the CO conversion as a function of time being on stream (hrs). Other admixed catalyst samples were tested and were comparable to Catalyst 5 Admixed and not shown here for clarity. Having greater than 70 wt % metal catalyst appears to provide comparable results to the reference admixed sample. Additional experiments were conducted with other acid catalysts. However, ZSM-5 was the best for co-extrusion under the reaction conditions tested.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. A method comprising:
mixing an acid catalyst, a metal catalyst, a binder, and a fluid to produce a dough, the acid catalyst comprising a zeolite, an ion exchanged zeolite, a molecular sieve, or a combination thereof, the metal catalyst comprising Cu, Zn, and Al;
extruding the dough to form an extrudate, the extruding being performed while heating the dough to a temperature within 20° C. of the boiling point of the fluid, the acid/metal bifunctional catalyst comprising 70 wt % to 80 wt % of the acid catalyst relative to a total weight of catalyst in the dough;
drying the extrudate;
producing a powder from the extrudate; and
calcining the powder to produce an acid/metal bifunctional catalyst.

2. The method claim 1, wherein producing the powder from the extrudate comprises:
grinding the extrudate before or after drying, wherein the powder comprises 5 wt % or less of the fluid.

3. The method of claim 1 further comprising:
drying the powder.

4. The method of claim 1, wherein the binder is selected from the group consisting of clay, theta-alumina, delta-alumina, alpha-alumina, silica, titania, zirconia, boric acid, carbon, and any combination thereof.

5. The method of claim 1, wherein the binder is present at 10 wt % to 80 wt % relative to the total solids weight in the dough.

6. The method of claim 1, wherein a weight ratio of the acid catalyst and the metal catalyst combined to the binder in the dough is about 10:1 to about 1:10.

7. The method of claim 1, wherein the fluid is selected from the group consisting of: water, methanol, ethanol, and any combination thereof.

8. The method of claim 1, wherein calcining is performed in air at 200° C. to 400° C.

9. The method of claim 1, wherein the acid/metal bifunctional catalyst has an average diameter of 0.01 µm to 100 µm.

10. The method of claim 1 further comprising:
activating the acid/metal bifunctional catalyst in the presence hydrogen at 150° C. to 350° C.; and
reacting the activated acid/metal bifunctional catalyst with a feedstream comprising hydrogen and carbon monoxide.

11. The method of claim 10, wherein reacting is at a temperature of about 200° C. to about 300° C., a pressure of about 20 bar to about 50 bar, and a gas hourly space velocity (GHSV) of about 1,000 $hr^{-1}$ to about 8,000 $hr^{-1}$.

12. The method of claim 10, wherein the reacting the activated acid/metal bifunctional catalyst with the feedstream is in the presence of steam.

\* \* \* \* \*